United States Patent [19]
Borden et al.

[11] Patent Number: 4,825,094
[45] Date of Patent: Apr. 25, 1989

[54] REAL TIME PARTICLE FALLOUT MONITOR WITH TUBULAR STRUCTURE

[75] Inventors: Peter Borden, Palo Alto; Jon Munson, Sunnyvale, both of Calif.

[73] Assignee: High Yield Technology, Mountain View, Calif.

[21] Appl. No.: 152,198

[22] Filed: Feb. 4, 1988

[51] Int. Cl.⁴ ............................................. G01N 15/06
[52] U.S. Cl. ..................................... 250/573; 356/338
[58] Field of Search ........................ 356/38, 335–343, 356/438, 439, 244, 246; 340/627, 630; 250/573, 576, 222.2, 222.1, 22.1, 239; 377/53

[56] References Cited
U.S. PATENT DOCUMENTS

| 3,708,675 | 1/1973 | Tashiro et al. | 340/630 |
| 3,922,656 | 11/1975 | Horvath et al. | 250/573 |
| 4,155,653 | 5/1979 | San Miguel et al. | 340/630 |
| 4,474,472 | 10/1984 | Winter | 356/38 |
| 4,748,336 | 5/1988 | Fujie et al. | 250/573 |

OTHER PUBLICATIONS

William C. Hinds, "Aerosol Technology", John Wiley & Sons, 1982, pp. 341–344.

Primary Examiner—David C. Nelms
Assistant Examiner—Michael Messinger
Attorney, Agent, or Firm—Skjerven, Morrill, MacPherson, Franklin & Friel

[57] ABSTRACT

An apparatus for monitoring particle fallout incorporates a particle flux monitor and a tubular structure. The tubular structure is positioned over an aperture in the housing of the monitor to provide a still air condition so that the particles that descend to the monitor and pass through the light net of the monitor are precluded from being carried back to the light net, which would result in an erroneous count.

9 Claims, 2 Drawing Sheets

REAL TIME PARTICLE FALLOUT MONITOR WITH TUBULAR STRUCTURE

FIELD OF THE INVENTION

This invention relates to a monitor for sensing particle fallout, particularly during the manufacture of products which are sensitive to contamination.

BACKGROUND OF THE INVENTION

Description of the Prior Art

Particle fallout generally occurs when large particles, typically greater than 5-10 microns in diameter, are deposited on the surfaces of processing equipment or the materials being processed. Such particles take the form of skin flakes, threads from clothing, or debris from operating machinery that may settle out, by way of example. Particle fallout may adversely affect contamination-sensitive processes and products. For example, in the assembly of sensitive components for satellites, excessive particle fallout can lead to failures after launch. Also, particles of this type can adversely affect manufacturing processes and the yield of products, such as printed circuit boards and hybrids.

Particle detectors are used to monitor levels of particulates that are present in a manufacturing environment, such as a semiconductor wafer processing system. The detected particulate level or count is used to localize and control the source of problems that occur during manufacturing processes in order to obtain optimum yields in the production of contamination-sensitive devices such as integrated circuits.

Optical particle counters are described in the textbook "Aerosol Technology" by William C. Hinds, published by John Wiley & Sons, 1982, at pages 341-344:

"As shown in FIG. 16.18 of this reference, air is drawn through a sensitive volume. This air carries particles that can be detected using light scattering as they pass through the sensitive volume. However, large particles do not remain effectively suspended in air and cannot efficiently negotiate the long length of tubing required to bring the air from the point in the environment to be sampled to the sensitive volume in the optical particle counter. As a consequence, the efficiency of this instrument becomes very low for particles larger in size than 10 microns. This is illustrated in Table 16.3 of the same reference, which shows that the upper limit of the effective size range is around 10 microns."

One type of particle detector that may be used for detection of spurious particles is disclosed in copending application Ser. No. 06/907,776, which issued Apr. 19, 1988, as U.S. Pat. No. 4,739,177, and is incorporated hereby by reference. The referenced patent discloses a particle detector for semiconductor wafer processing equipment wherein a light beam is employed that is reflected multiple times between mirrors to form a light sheet. Particles traversing the light sheet cause light to scatter, and the scattered light is detected by photosensing means.

In the particle flux monitor described in the referenced patent, particles having a diameter up to several millimeters are detected in real time. However, many fallout particles do not fall or drop straight down but are carried by air currents as they proceed to fall. Therefore, air currents that occur close to the sensor device can draw particles, such as skin flakes, through the sensor that do not necessarily fall onto a surface of the unit in production or onto contamination-sensitive manufacturing equipment. As a result, the sensor will count many more particles than those that actually fall out and impinge on the contamination-sensitive surface.

In one approach, witness plate methods are applied to monitor particle fallout. A flat plate is placed at a critical location to collect fallout over a period of time. The plate is then viewed under a microscope and the particles are counted. This technique is not implemented in real time and in effect indicates only when a fallout generating event has previously occurred. Furthermore, the technique is labor intensive, subject to human error and difficult to automate.

It is highly desirable to be able to rapidly find the active sources of the particle fallout to allow steps to be taken to correct the problem and control fallout levels before serious damage occurs.

SUMMARY OF THE INVENTION

An object of this invention is to provide a particle fallout monitor that can detect relatively large particles in a manufacturing environment in real time which will enable quick control of particle fallout levels.

Another object of this invention is to provide a particle fallout monitor that allows determination of the rates of fallout of generated particles in a manufacturing environment.

Another object is to provide a fallout monitoring means that is capable of real-time data collection whereby immediate warning is obtained of deleterious particle fallout conditions.

Another object is to provide a real time data collection system for counting particles that enables coupling to a computerized data collection and analysis system thereby minimizing labor requirements.

According to this invention, a particle flux monitor for sensing fallout particles in an environment wherein such particles may descend onto a contamination-sensitive surface comprises means for producing a light net and sensing means for detecting light scattered by particles falling through the light net. A tubular structure is attached to the particle flux monitor at an opening on the surface of the monitor housing. The aerodynamic characteristics produced by the provision of the tubular structure ensures that a substantially static air condition exists at the bottom of the tubular structure. As a result, particles descend to the monitor and are not moved in and out of the light net, thus ensuring that only particles that descend and settle are counted.

DESCRIPTION OF THE DRAWINGS

The invention will be described in greater detail with reference to the drawing in which.

DETAILED DESCRIPTION OF THE INVENTION

Figure 1:
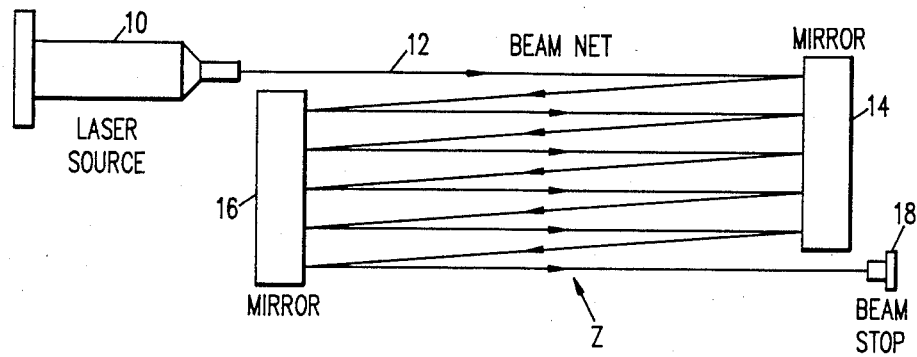
FIG. 1 is a side view of a particle flux monitor used for detecting particles appearing in a light net.

FIG. 1 depicts a configuration of an optical system that is employed with a particle flux monitor, in accordance with this invention. A light source 10, such as a laser, provides a light beam 12 to a mirror 14 which reflects the beam to a second mirror 16. The light beam is reflected several times between the mirrors to form a light net 2. The beam is finally reflected to a beam stop 18. Light that is scattered by particles that appear within the light net is sensed by a pair of photosensors 22 (see FIG. 2) which are electrically connected and the signal generated by the photosensors is amplified in an amplifier 24 and applied to a data processor 26.

Figure 2:
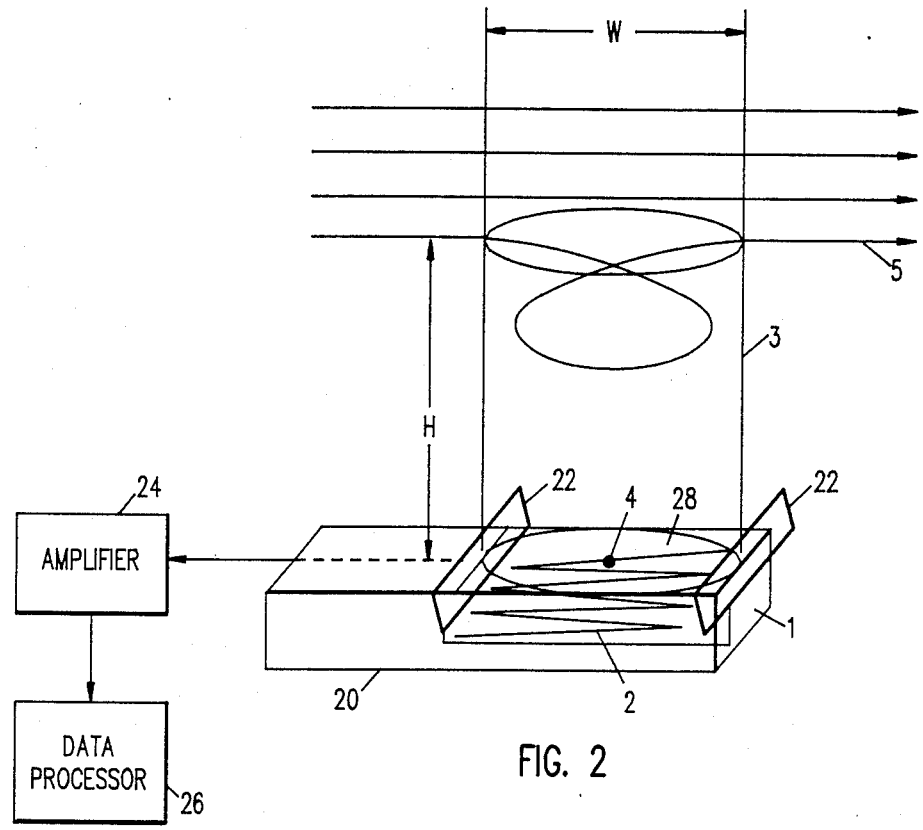
FIG. 2 is an isometric view of the particle fallout monitor, in accordance with this invention.

As shown in FIG. 2, a particle flux monitor 1 which includes the elements of the optical configuration of FIG. 1 is enclosed by a housing or enclosure 20 wherein the light net 2 is generated. Light detectors or photosensors 22 are positioned adjacent to the light net to receive light scattered by any particle 4 that passes within the light net. The photosensors 22 generate a signal in response to the scattered light and the generated signal is amplified and processed by the data processor or computer 26. The processor collects and analyzes the data and thereby provides a warning if the magnitude of particle fallout is greater than a specified level.

In accordance with this invention, a tubular structure 3, which is open at the top and bottom, is seated or attached to the housing 20 of the particle flux monitor 1. The tubular structure surrounds an opening 28 formed on the surface of the housing 20. The lateral air flow pattern in the interior of the tubular structure is indicated by the arrows or stream lines 5. It is known that an air flow passing an opening will create a turbulent flow that occurs near the top of the opening of the tubular structure, in accordance with the principles of aerodynamics. The air flow at the bottom of the tubular structure which is seated on the enclosure 20 will be relatively still and virtually static. The air flow pattern within the tubular structure 3 prevents the particles from being transported in and out of the light net 2 so that only settling particles are sensed and counted.

Figure 3:
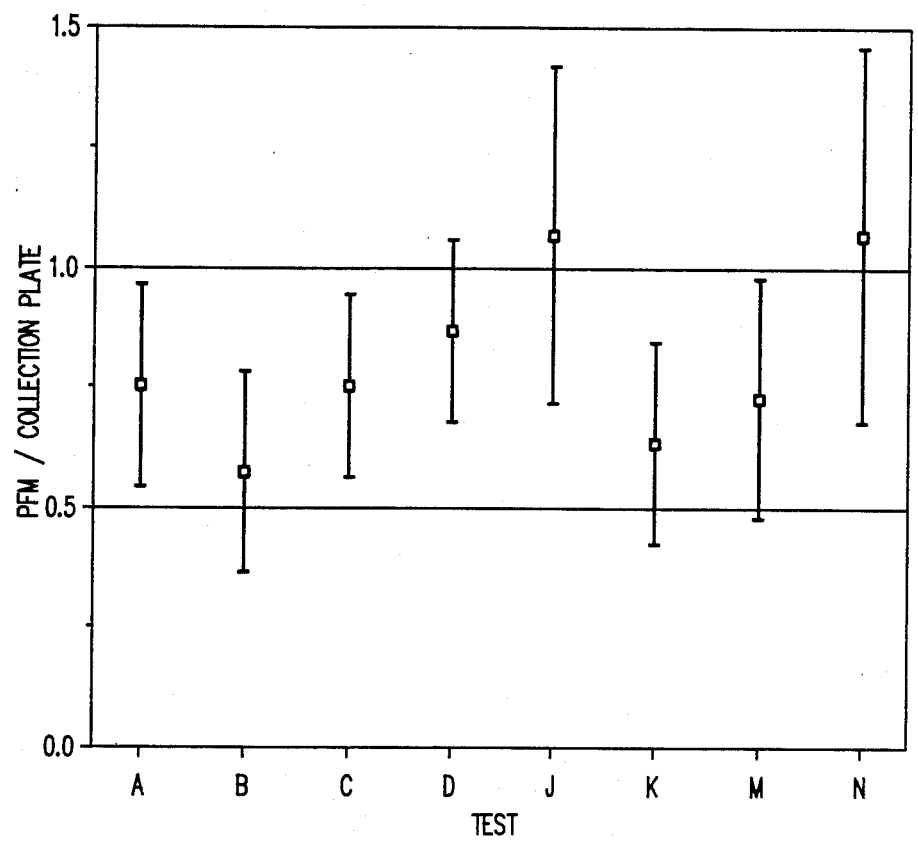
FIG. 3 is a table illustrating the ratio of particle counts by the particle fallout monitor to the particle counts using collection plate techniques for various air flow conditions.

In practice, the assembly of the particle flux monitor and tubular structure of this invention is placed within the manufacturing environment to be tested, which may be where a workpiece or semiconductor wafer is to be processed, for example. In a series of tests and experiments employing the assembly of the monitor and tubular structure under different air flow conditions, a collection plate was placed at the bottom of the particle flux monitor to collect particles that had descended through the tubular structure to the particle flux monitor. FIG. 3 is a plot of the ratio of the number of particles counted by the particle flux monitor to the number of particles counted on the collection plate with the aid of a microscope. It has been observed that this ratio remains consistently at about 0.75 for various air flows.

The following Table 1 is a listing of the air flow conditions of the tests that were conducted, indicating the number of particles collected per hour on the collection plate and the duration of the test.

TABLE 1

| Test | Air Flow | Plate Cts/Hr. | Duration (hours) |
| --- | --- | --- | --- |
| A | Still | 3.7 | 17:43 |
| B | Lateral 50 ft/min | 1.5 | 23:03 |
| C | Lateral 100 ft/min | 3.3 | 23:05 |
| D | Vertical 75 ft/min | 5.0 | 16:08 |
| J | Lateral 50 ft/min | 1.1 | 38:00 |
| K | Lateral 100 ft/min | 2.6 | 22:00 |
| M | Still | 0.64 | 66:39 |
| N | Still (see note) | 0.44 | 66:39 | note:
In test N, the plate was placed next to the sensor rather than under the sensor. Tests M and N were run at the same time in the same location.

In an implementation of this invention, the tubular structure was made of aluminum tubing, with a height of at least 3 inches approximately and a width or diameter of about 1.5 inches. The ratio of height to width is preferably greater than 2 for proper air flow conditions in the tubular structure. It should be understood that the tubular structure can be cylindrical, rectangular or formed in a different geometrical configuration, and can be made of different materials to provide the desired air flow conditions adjacent to the light net in accordance with this invention.

What is claimed is:

1. An assembly for monitoring particle fallout comprising:
    particle flux monitoring means including a housing with an aperture on a major surface, said housing having a closed surface opposite to said major surface to provide an effective closure; and
    a tubular structure seated on said major surface having its top end open and its bottom end disposed over said aperture and facing said effective closure for providing a substantially static air condition adjacent to said aperture so that particles descend through said tubular structure to land and settle on said opposite surface.

2. An assembly as in claim 1 wherein the height of said tubular structure is at least twice the width or diameter of said tubular structure.

3. An assembly as in claim 1 wherein said tubular structure is made of aluminum tubing.

4. An assembly as in claim 1 wherein said monitoring means comprises means for providing a light net within said housing below said aperture.

5. An assembly as in claim 4 wherein said monitoring means includes a photosensing means within said housing adjacent to said light net for generating a signal in response to scattered light.

6. An assembly as in claim 5 including an amplifier coupled to said photosensing means for amplifying the signal generated by said photosensing means.

7. An assembly as in claim 6, including a data processor coupled to said amplifier for correcting and analyzing data corresponding to the signal generated by said photosensing means.

8. An assembly as in claim 7 wherein said data processor operates in real time to detect the appearance of particles that traverse said light net.

9. An assembly as in claim 1 wherein said tubular structure is cylindrical, rectangular or elliptical.

* * * * *